(12) United States Patent
Edwards et al.

(10) Patent No.: US 7,179,299 B2
(45) Date of Patent: Feb. 20, 2007

(54) OSTEOIMPLANT AND METHOD FOR MAKING SAME

(75) Inventors: Jean T. Edwards, Waconia, MN (US); Lawrence A. Shimp, Morganville, NJ (US); Michele Diegmann, Scotch Plains, NJ (US); Todd M. Boyce, Aberdeen, NJ (US); Nelson L. Scarborough, Andover, MA (US); James L. Russell, Little Silver, NJ (US)

(73) Assignee: Osteotech, Inc., Eatontown, NJ (US)

( * ) Notice: Subject to any disclaimer, the term of this patent is extended or adjusted under 35 U.S.C. 154(b) by 0 days.

(21) Appl. No.: 10/285,715

(22) Filed: Nov. 1, 2002

(65) Prior Publication Data
US 2003/0144743 A1 Jul. 31, 2003

Related U.S. Application Data

(63) Continuation of application No. PCT/US01/15599, filed on May 14, 2001, and a continuation-in-part of application No. 09/328,242, filed on Jun. 8, 1999, now Pat. No. 6,277,149.

(60) Provisional application No. 60/221,056, filed on Jul. 27, 2000, provisional application No. 60/204,069, filed on May 12, 2000.

(51) Int. Cl.
*A61F 2/28* (2006.01)
(52) U.S. Cl. .................. 623/23.61; 623/23.61
(58) Field of Classification Search .. 623/17.11–16.11, 623/23.61, 23.63
See application file for complete search history.

(56) References Cited

U.S. PATENT DOCUMENTS

| | | | | |
|---|---|---|---|---|
| 5,298,254 | A | * | 3/1994 | Prewett et al. ............... 424/422 |
| 5,899,939 | A | | 5/1999 | Boyce et al. |
| 6,090,998 | A | * | 7/2000 | Grooms et al. ............. 128/898 |
| 6,123,731 | A | * | 9/2000 | Boyce et al. ............. 623/23.63 |
| 6,206,923 | B1 | * | 3/2001 | Boyd et al. ............... 623/17.11 |
| 6,277,149 | B1 | * | 8/2001 | Boyle et al. ............. 623/17.16 |
| 6,340,477 | B1 | * | 1/2002 | Anderson .................... 424/488 |
| 6,425,920 | B1 | * | 7/2002 | Hamada ................... 623/17.16 |
| 6,458,375 | B1 | * | 10/2002 | Gertzman et al. .......... 424/423 |
| 2002/0016633 | A1 | * | 2/2002 | Lin et al. .................. 623/17.11 |
| 2002/0120338 | A1 | * | 8/2002 | Boyer et al. ............. 623/17.19 |
| 2003/0083747 | A1 | * | 5/2003 | Winterbottom et al. .. 623/17.11 |

FOREIGN PATENT DOCUMENTS

| | | |
|---|---|---|
| WO | W0 99/21515 | 5/1999 |
| WO | WO 99/21515 * | 5/1999 |
| WO | WO 99/39757 | 8/1999 |

* cited by examiner

*Primary Examiner*—Eduardo C. Robert
*Assistant Examiner*—Annette R. Reimers
(74) *Attorney, Agent, or Firm*—Dorsey & Whitney, LLP

(57) ABSTRACT

A method of manufacturing an osteoinductive osteoimplant is provided which comprises the steps of: demineralizing part or all of at least one surface of a monolithic section of cortical bone to a depth of at least about 100 microns; and, configuring the monolithic section of cortical bone to provide an osteoimplant possessing an outer surface possessing at least one demineralized zone and a non-demineralized zone. An implant produced according to the above method demonstrates improved osteoinduction without producing any clinically significant reduction of strength in critical regions of the osteoimplant.

34 Claims, 7 Drawing Sheets

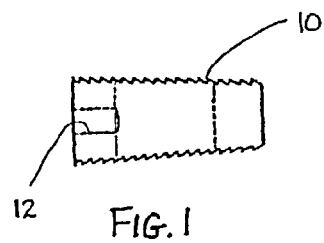
FIG. 1
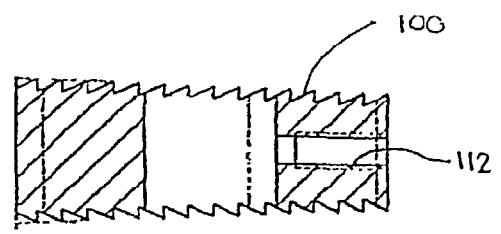
FIG. 3
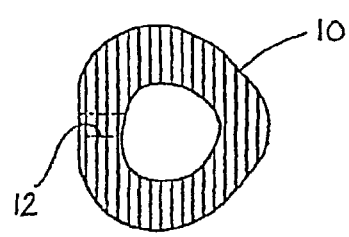
FIG. 2
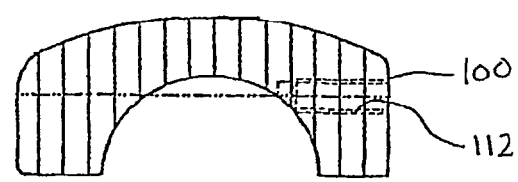
FIG. 4
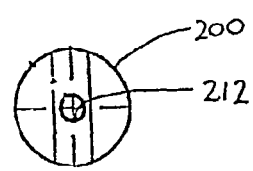
FIG. 5
FIG. 7
FIG. 8
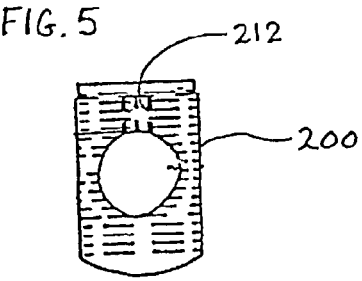
FIG. 6

OSTEOIMPLANT AND METHOD FOR MAKING SAME

CROSS-REFERENCE TO RELATED APPLICATIONS

This is a continuation of co-pending application Ser. No. PCT/US01/15599 filed in English on May 14, 2001 and which claims benefit under 35 U.S.C. §119(e) of Provisional Appln. Ser. Nos. 60/204,069 and 60/221,056 respectively filed May 12, 2000 and Jul. 27, 2000, and a continuation-in-part of U.S. application. Ser. No. 09/328,242 filed Jun. 8, 1999 and now U.S. Pat. No. 6,277,149 issued Aug. 21, 2001, the entire contents of all of which are incorporated herein by this reference.

BACKGROUND OF THE INVENTION

1. Field of the Invention

The present disclosure is directed to a method for preparing a partially demineralized bone graft. More specifically, this invention relates to a load-bearing osteogenic osteoimplant fabricated from a monolithic section of cortical bone and to a method for making the osteoimplant as well as a method of using same.

2. Description of the Related Art

Shaped or cut bone segments have been used extensively to solve various medical problems in human and animal orthopedic surgical practice and their application has also extended to the field of cosmetic and reconstructive surgery, dental reconstructive surgery, and other medical fields involving surgery of hard tissues. The use of autograft bone (where the patient provides the source), allograft bone (where another individual of the same species provides the source), xenograft bone (where another individual of a different species provides the source) or transgenic bone (where a transgenic species provides the source) is well known in both human and veterinary medicine. In particular, transplanted bone is known to provide support, promote healing, fill bony cavities, separate bony elements (such as vertebral bodies), promote fusion (where bones are induced to grow together into a single, solid mass), or stabilize the sites of fractures. More recently, processed bone has been developed into shapes for use in new surgical applications, or as new materials for implants that were historically made of non-biologically derived materials.

Osteoimplants come in a variety of shapes and sizes including cut cross-sections, cylindrical dowels, cortical rings, elongated struts, wedges, blocks, screws, pins, etc., as well as assembled implants made of two or more bone pieces such as, for example, described in U.S. Pat. No. 5,899,939 to Boyce et al., U.S. Pat. No. 6,025,538 to Yaccarino, III, U.S. Pat. No. 6,123,731 to Boyce et al., and U.S. Pat. No. 6,200,347 B1 to Anderson et al., the contents of each being incorporated herein by reference. Osteoimplants are used in a variety of different surgical procedures including bone fracture repair, spinal fusion procedures, tendon repair, cosmetic surgery, etc. Typically, osteoimplants will include engagement structure formed integrally therein for detachable engagement of an implant insertion tool to facilitate insertion of the osteoimplant into an implant site. Such engagement structure may include a threaded bore, multiple bore holes, a hexagonal recess, an irregular shape recess, etc. For accurate insertion of the osteoimplant at the surgical site, it is important that close tolerances be maintained between the implant insertion tool and the engagement structure of the osteoimplant.

Bone grafting applications are differentiated by the requirements of the skeletal site. Certain applications require a "structural graft" in which one role of the graft is to provide mechanical or structural support to the site. Such grafts contain a substantial portion of mineralized bone tissue to provide the strength needed for load-bearing. Examples of applications requiring a "structural graft" include intercalary grafts, spinal fusion, joint plateaus, joint fusions, large bone reconstructions, etc. Other applications require an "osteogenic graft" in which one role of the graft is to enhance or accelerate the growth of new bone tissue at the site. Such grafts contain a substantial portion of demineralized bone tissue to improve the osteoinductivity needed for growth of new bone tissue. Examples of applications requiring "osteogenic graft" include deficit filling, spinal fusions, joint fusions, etc. Grafts may also have other beneficial biological properties, such as, for example, serving as delivery vehicles for bioactive substances. Bioactive substances include physiologically or pharmacologically active substances that act locally or systemically in the host.

When mineralized bone is used in osteoimplants, it is primarily because of its inherent strength, i.e., its load-bearing ability at the recipient site. The biomechanical properties of osteoimplants upon implantation are determined by many factors, including the specific site from which the bone used to make the osteoimplant is taken; the age, sex, and physical characteristics of the donor; and the method chosen to prepare, preserve, and store the bone prior to implantation, as well as the type of loading to which the graft is subjected.

Structural osteoimplants are conventionally made by processing, and then machining or otherwise shaping cortical bones collected for transplant purposes. Cortical bone can be configured into a wide variety of configurations depending on the particular application for the structural osteoimplant. Structural osteoimplants are often provided with intricate geometries, e.g., series of steps; concave or convex surfaces; tapered surfaces; flat surfaces; surfaces for engaging corresponding surfaces of adjacent bone, tools, or implants, hex shaped recesses, threaded holes; serrations, etc.

One problem associated with many structural osteoimplants is that they are never fully incorporated by remodeling and replacement with host tissue. This is due, in part, to the difficulty with which the host's blood supply may penetrate cortical bone. Moreover, non-demineralized bone is not osteoinductive. Since repair is a cellular-mediated process, dead (non-cellular, allograft or xenograft) bone is unable to repair itself. When the graft is penetrated by host cells and host tissue is formed, the graft is then capable of repair. It has been observed that fatigue damage is usually the result of a buildup of unrepaired damage in the tissue. Therefore, to the extent that the implant is incorporated and replaced by living host bone tissue, the body can then recognize and repair damage, thus eliminating failure by fatigue. In applications where the mechanical load-bearing requirements of the osteoimplant are challenging, e.g., intervertebral spinal implants for spinal fusion, lack of substantially complete replacement by host bone tissue may compromise the osteoimplant by subjecting it to repeated loading and cumulative unrepaired damage in the tissue (mechanical fatigue) within the implant material. Thus, it is highly desirable that the osteoimplant has the capacity to support load initially and be capable of gradually transferring this load to the host bone tissue as it remodels the implant.

As stated above, a known technique for promoting the process of incorporation of osteoimplants is demineralization. The process of demineralizing bone grafts is well known. In this regard see, Lewandrowski et al., *J. Biomed Materials Res*, 31, pp. 365–372 (1996); Lewandrowski et al., *Calcified Tiss. Int.*, 61, pp. 294–297 (1997); Lewandrowski et al., *J. Ortho. Res.*, 15, pp. 748–756 (1997), the contents of each of which is incorporated herein by reference. However, the prior art has not addressed the need to provide a demineralized osteoimplant with sufficiently mineralized regions for engagement of insertion instrumentation.

Demineralizing bone, using for example, a controlled acid treatment, increases the osteoinductive characteristics of the osteoimplant. Demineralization also provides the osteoimplant with a degree of flexibility. However, removal of the mineral components of bone significantly reduces mechanical strength of bone tissue. See, Lewandrowski et al., *Clinical Ortho. Rel. Res.*, 317, pp. 254–262 (1995). Thus, demineralization sacrifices some of the load-bearing capacity of mineralized cortical bone and as such is not suitable for all osteoimplant designs. Another disadvantage to the demineralization process is the likelihood of creating dimensional changes in the osteoimplant. Demineralization of the bone will ordinarily result in bone of slightly smaller dimensions. Such changes of dimension can make it difficult for a configured piece to mechanically engage with surgical instruments, other implants, or the prepared surgical site.

Accordingly, a need exists for an improved process for demineralizing an osteoimplant to achieve an improved biologic response to the implant while maintaining a mineralized portion of the osteoimplant that can endure mechanical forces and/or maintain close tolerances with insertion instrumentation and/or the implant site. Complete mineralization may be especially important for portions of an osteoimplant experiencing the greatest mechanical loads such as engagement structure of the osteoimplant. In certain embodiments, these areas are masked from the demineralization process. In other embodiments, a demineralized portion of the osteoimplant is removed by, for example, configuring, to expose the mineralized portion beneath the demineralized surface region.

It would be advantageous if a surface demineralized load-bearing osteoinductive osteoimplant could be achieved efficiently and accurately by a simple process. Use of such an osteoimplant in a load-bearing procedure such as, for example, joint plateau revisions, joint fusions, spinal fusions, long bone reconstructions, etc. would provide a favorable outcome for the recipient of the implant.

BRIEF SUMMARY OF THE INVENTION

A method of manufacturing a surface demineralized osteoinductive osteoimplant is provided which comprises the steps of: demineralizing part or all of at least one surface of a monolithic section of bone to a depth of at least about 100 microns; and, configuring the monolithic section of bone to provide an osteoimplant possessing an outer surface possessing at least one demineralized zone and at least one non-demineralized zone.

An implant produced according to the above method demonstrates improved osteoinduction without producing any undesirable clinically significant reduction of strength. Further embodiments of the above method provide for methods of configuring, for example, cutting, machining, or shaping the osteoimplant, either before and/or after demineralization to provide an osteoimplant having desirable characteristics depending upon the intended application. Yet even further embodiments of the method herein provided for selective masking of regions of the bone prior to demineralization to prevent any undesirable changes in certain dimensions of the bone as well as to provide the ability to tailor the osteoinductive/load-bearing characteristics of specific portions of the osteoimplant depending upon the intended use of the osteoimplant. An implant prepared in accordance with this embodiment also provides a mineralized zone and a demineralized zone, however, a mineralized zone will be presented on the surface of the implant as well as in the inner core of the implant.

Also provided is a surface demineralized osteoinductive osteoimplant made of a monolithic section of bone that has at least one outer surface possessing at least one demineralized zone and a non-demineralized core, wherein the demineralized zone of the outer surface of the bone is at least about 100 microns thick.

Also provided is a vertebral interbody fusion device made of a monolithic section of bone configured to span an intervertebral space between adjacent vertebrae or an intervertebral space spanning non-adjacent vertebrae, in which the bodies of the intervening vertebrae are replaced in their supportive function by the graft. The bone has at least one outer surface with at least one demineralized zone for contacting the adjacent vertebra. The bone also has a non-demineralized core to provide for load-bearing. The demineralized zone of the outer surface of the bone is at least about 100 microns thick.

Also provided is a method of promoting joint fusion in an animal in need thereof. The method involves implanting in the animal a load-bearing osteoinductive osteoimplant made of bone having an outer surface possessing at least one demineralized zone and a non-demineralized zone. The demineralized zone of the outer surface of the bone is at least about 100 microns thick.

Also provided is a method of treating a bone defect in an animal in need thereof. The method consists of applying an osteoinductive osteoimplant made of bone having an outer surface possessing at least one demineralized zone and a non-demineralized zone. The demineralized zone of the outer surface of the bone is at least about 100 microns thick. The osteoimplant is applied to the defect site such that the surface of the osteoimplant conforms to the surface of the bone defect site.

Also provided is a osteoimplant implantation kit containing an osteoimplant and a delivery tool useful in performing the placement of the osteoimplant during a surgical procedure. The osteoimplant may be provided in a presterillzed, prepackaged form held by the delivery tool, which can be used without repositioning the osteoimplant in the tool. The implantation tool carries the osteoimplant so as to avoid damage to the osteoimplant prior to and during surgical implantation. The tool also permits the surgeon to securely hold the osteoimplant during implantation and to easily place it at the proper location.

BRIEF DESCRIPTION OF THE SEVERAL
VIEWS OF THE DRAWINGS

The FIGS. 1–6 represent different non-limiting examples of osteoimplants.

FIGS. 1 and 2 illustrate a tapered osteoimplant made from a long bone diaphysis, e.g., femoral ring, shown generally as 10.

FIGS. 3 and 4 illustrate a tapered osteoimplant made from a segment taken from a partial ring shown generally as 100.

FIGS. 5 and 6 illustrate a cylindrical threaded dowel osteoimplant shown generally as 200. Each of the above osteoimplants includes engagement structure 12, 112, 212 for engaging an insertion tool to facilitate insertion of the osteoimplant into an implant site.

FIGS. 7 and 8 illustrate various components that can be used to physically mask portions of the osteoimplant during demineralizing.

DETAILED DESCRIPTION OF THE INVENTION

Figure 9:
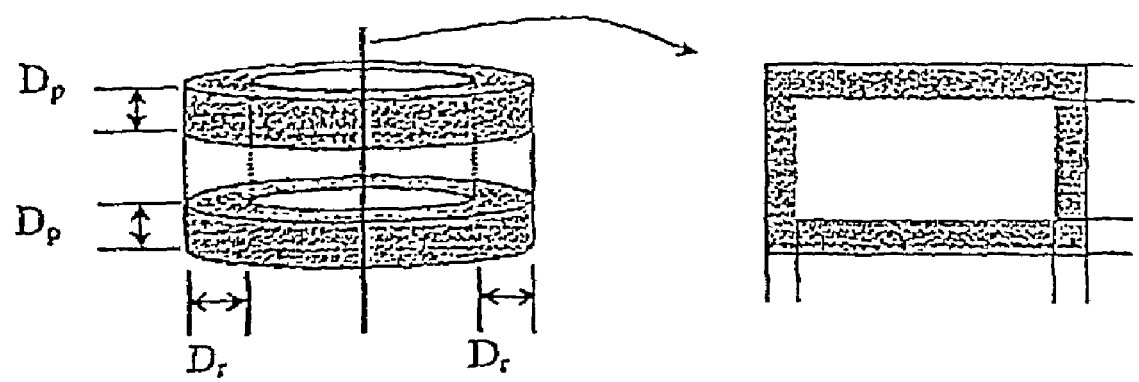
FIGS. 9 and 10 illustrate the experimental method used to determine the histomorphometry of bone used in the osteoimplant described herein.

The below definitions are intended to be understood in the broadest sense unless otherwise specified and serve to provide a clear and consistent understanding of the specification and claims, including the scope to be given such terms.

The term "configuring" as utilized herein refers to any method of mechanically or chemically changing the spatial appearance or conformation of an osteoimplant without limitation as to the specific apparatus employed. Therefore, methods of configuring would include a variety of operations, for example, cutting, shaving, slicing, milling, grinding, drilling, molding, shaping, turning, chiseling, dissolving, etching, etc. Thus, any and all possible methods of configuring are envisioned as being within the scope of the disclosure herein.

The expression "clinically significant" as utilized herein refers to the absence of any undesirable reduction in strength likely to cause a negative outcome in a patient having an osteoimplant as described herein placed at an implant site. It is to be understood that some reduction in strength is to be expected in any portion of bone that is demineralized. However, such reduction of strength according to the method herein would be expected to improve the biological response of a patient, for example, by improving conformability of the osteoimplant to the implant site. Such improved biological response will be discussed in greater detail in a later section of this disclosure.

The term "osteoimplant" as utilized herein is intended to refer to any device or material for implantation that aids or augments bone formation or healing. Osteoimplants are often applied at a bone defect site, e.g., one resulting from injury, defect brought about during the course of surgery, infection, malignancy or developmental malformation. Therefore, such "osteoimplants" are envisioned as being suitably sized and shaped as required for use in a wide variety of orthopedic, neurosurgical, and oral and maxillofacial surgical procedures such as the repair of simple and compound fractures and non-unions, external and internal fixations, joint reconstructions such as arthrodesis, general arthroplasty, deficit filling, discectomy, laminectomy, anterior cervical and thoracic operations, spinal fusions, etc. Therefore, the osteoimplants utilized herein are intended for implantation at a bony site and are made of any substantially monolithic bone and may be designed for either animal or human use. Specifically, the osteoimplant suitable for use according to the disclosure herein will be any osteoimplant substantially fabricated from a monolithic section of bone.

The expression "monolithic bone" as utilized herein refers to relatively large pieces of human or animal bone, i.e., pieces of bone, autograft, allograft, xenogenic, or transgenic, that are of such size and composition as to be capable of withstanding the sort of mechanical loads to which functioning bone is characteristically subjected, e.g., cortical bone. It is further to be understood that the expression "monolithic bone" refers to fully mineralized bone, i.e., bone with its full natural level of mineral content, and to such bone that has been demineralized to some minor extent, i.e., to an extent which reduces the original mechanical strength of the bone by no more than about 50 percent. The monolithic bone can be provided as a single integral piece of bone, preferably corticocancellous bone, more preferably cortical bone or as a piece of bone permanently assembled from a number of smaller bone elements such as, for example, composite bone and/or assembled bone as described in U.S. Pat. Nos. 5,899,939, 6,025,538, 6,123,731, 6,200,347, the contents of each being incorporated herein by reference. Although monolithic bone can contain factors that are osteogenic, monolithic bone can also contain additional materials, e.g., as disclosed in U.S. Pat. No. 5,290,558 the contents of which are incorporated herein by reference, which will remain with the bone after its rehydration and will be present at the time of implantation. Monolithic bone can therefore include autograft, allograft, xenogenic, and transgenic material as well as mixtures thereof. Because bone itself contains small pores or channels, the monolithic bone useful herein can likewise contain pores or channels whether naturally occurring or formed by mechanical means, e.g., drilling, laser machining, etc.

The term "load-bearing" as utilized herein shall be understood as meaning capable of supporting a force as is typically applied at an implant site. The osteoimplant described herein will be considered to be load-bearing even if portions of the implant, e.g., demineralized regions, are deformed by the force applied at an implant site. Of course it will be understood by those skilled in the art that all materials are potentially deformable by forces. However, the magnitude of deformation as a result of the same force being exerted upon a mineralized and demineralized bone would differ greatly and might not be easily measurable in the mineralized bone.

The expression "engaging regions" and expressions of like import will be understood as referring to those regions of the osteoimplant that are substantially mineralized, either by masking before demineralizing and/or configuring a demineralized region to expose a mineralized portion beneath, and are intended to reversibly connect with the attachment portion of an insertion tool or remain in sustained contact with another implant or implant device at the surgical site.

The term "biocompatible" and expressions of like import shall be understood to mean the absence of stimulation of an unacceptable biological response to an implant and is distinguished from a mild, transient inflammation and/or granulation response which can accompany implantation of most foreign objects into a living organism and is also associated with the normal healing response. Materials useful to the invention herein shall be biocompatible if, at the time of implantation, they are present in a sufficiently small concentration such that the above-defined condition is achieved.

The term "autograft" as utilized herein refers to tissue that is extracted from the intended recipient of the implant. Such material will be considered to be autograft even when prepared in tissue culture.

The term "allograft" as utilized herein refers to tissue intended for implantation that is taken from a different member of the same species as the intended recipient.

The term "xenogenic" as utilized herein refers to material intended for implantation obtained from a donor source of a different species than the intended recipient. For example, when the implant is intended for use in an animal such as a horse (equine), xenogenic tissue of, e.g., bovine, porcine, caprine, etc., origin may be suitable.

The term "transgenic" as utilized herein refers to tissue intended for implantation that is obtained from an organism that has been genetically modified to contain within its genome certain genetic sequences obtained from the genome of a different species.

The term "whole" as utilized herein refers to bone that contains its full mineral content.

The term "demineralized" as utilized herein refers to bone containing less than about 95% of its original mineral content.

The expression "fully demineralized" as utilized herein refers to bone containing less than about 5% of its original mineral content.

The term "acid" as utilized herein is intended to refer to any acid or mixture of acids capable of demineralizing bone, preferably hydrochloric acid. Other suitable acids include formic acid, acetic acid, peracetic acid, citric acid, propionic acid, other organic acids, etc. Suitable inorganic acids include the mineral acids hydrochloric acid, phosphoric acid, etc. Chelators such as ethylenediaminetetraacetic acid (EDTA) (or analogues of this chelator such as EGTA), citric acid, succinic acid, heparin, etc. can be used to chelate (bind) calcium which aids in the demineralization of bone by both organic and inorganic acids. Suitable ranges of acid concentration would vary depending upon the strength of the acid (its ability to disassociate the mineral salts found in bone) and the temperature of the demineralizing solution and would range from about 0.1 molar to about 10 molar.

The term "osteogenic" as utilized herein shall be understood as referring to the ability of an osteoimplant to enhance or accelerate the growth of new bone tissue by one or more mechanisms such as osteogenesis, osteoconduction and/or osteoinduction.

The term "osteoinductive" as utilized herein shall be understood to refer to the ability of a substance to recruit cells from the host that have the potential for forming new bone and repairing bone tissue. Most osteoinductive materials can stimulate the formation of ectopic bone in soft tissue.

The term "osteoconductive" as utilized herein shall be understood to refer to the ability of a non-osteoinductive substance to serve as a suitable template or substrate along which bone may grow.

Bone is the hard form of connective tissue that constitutes the majority of the skeleton of most vertebrates. It consists of an organic component (the cells and matrix) and an inorganic, or mineral, component. In processing bone intended for implantation, the cellular component is frequently removed to reduce the antigenicity of the implant. The matrix contains a framework of collagenous fibers and non-collangenous proteins and is impregnated with the mineral component which imparts the quality of rigidity to the bone.

The mineralized component of the bone is largely contained within the cortical region of the bone. This region of the bone contains freely anastomosing channels that, in the native state, contain blood vessels, lymph vessels, and nerves. These channels are frequently referred to as Haversian canals.

As stated above, during preparation of bone intended for implantation, the cells are frequently removed. The removal of cells also results in the removal of tissues generally associated with the bone such as, for example, blood vessels, lymph vessels, nerves, etc. The initial processing of bone intended for implantation is known and described in U.S. Pat. Nos. 5,333,626, 5,513,662, and 5,846,484, the contents of each being incorporated herein by reference. The removal of these tissues results in the formation of substantially empty Haversian canals. This portion of the cortical bone, consisting of a Haversian canal and its concentrically arranged lamellae, is referred to as an osteon. The osteons are directed mainly in the long axis of the bone and are typically about 200 µm in diameter.

It has been discovered herein that surface demineralization of an osteoimplant to a depth just sufficient to expose the osteons provides an osteoimplant having the desirable combined characteristics of improved biological response of the osteoimplant while maintaining a mineralized core portion of the osteoimplant capable of sustaining mechanical loads such as those frequently encountered at an implant site. Although not entirely understood, it is believed that the improvement in the biological response is due to providing access to the Haversian system to allow cells such as, for example, osteoblasts, access to the mineralized core region of the osteoimplant. In addition, new chondrocytes can penetrate into demineralized Haversian canals of the demineralized region of the osteoimplant. It is believed that in this manner the Haversian system serves as the "seed" of osteoinductivity, thus allowing the implant to remodel from the inside out as well as the outside in. Of course, when desirable, small pores or canals can be mechanically introduced into the osteoimplant. For example, when the osteoimplant is an aggregate or composite structure, a variety of materials and methods can be used to introduce the pores or canals into the osteoimplant, e.g., small drill bits, a laser of suitable power and wavelength, water-jet cutters, hole-saws, etc. can be used to create appropriately dimensioned and configured passageways into the interior regions of the osteoimplant. Such passageways will typically have diameters between about 50 µm and about 1000 µm. Of course, larger holes in the millimeter size range might also be useful to assist with penetration of the osteoimplant with blood vessels, one of the early stages of bone incorporation.

The demineralized zone of the surface of the osteoimplant of this invention is osteoinductive, and therefore promotes rapid new ingrowth of native host bone tissue into the osteoimplant. The demineralized zone of the surface of the osteoimplant can be any surface portion. For example, when the osteoimplant is a femoral ring intended for implantation as a spinal fusion device, the demineralized zone of the surface can be limited to those surfaces intended to contact vertebra. When the osteoimplant is intended for a different application; e.g., intercalary grafting, where the cut surface of the graft mates with that of a long bone; onlay grafting, where the outer (endosteal, periosteal) or cut surface would be adjacent the periosteal surface of a bone; the adjacent portion of the osteoimplant can be the demineralized zone of the surface. In this manner the biological properties of the osteoimplant in relation to the graft receiving surface(s) can be improved.

When it is desirable to provide an osteoimplant having improved biological properties while still substantially maintaining the strength present in the osteoimplant prior to demineralization, the extent and regions of demineralization of the implant will be controlled. For example, the depth of demineralization must be at least about 100 microns but depths of demineralization ranging up to about 7000 microns or more may be entirely suitable depending on the intended application and graft site. Typically the depth of demineralization will be between 100 to about 5000 microns, preferably from about 150 to about 2000 microns, more preferably between about 200 microns to about 1000 microns. Any and all such variations and combinations of demineralized zone(s) of the surface of the osteoimplant as described above are therefore envisioned as being within the scope of the disclosure herein.

Another significant advantage of the demineralized zone(s) is the ability of demineralized bone to elastically yield under applied force. Thus, when the osteoimplant is subjected to an applied load at the site of implantation, the demineralized zones on the surface of the osteoimplant can conform to the contours of adjacent bone tissue and thereby minimize voids or spaces between the osteoimplant and adjacent bone tissue. This is important because host bone tissue will not grow to bridge large voids or spaces. Thus, by conforming to the contours of adjacent bone tissue, the osteoimplant of this invention exhibits enhanced biological properties such as, for example, incorporation and remodeling. The non-demineralized inner core of the osteoimplant imparts mechanical strength and allows the osteoimplant to bear loads in vivo. Other non-demineralized zones provide improved tolerances when engaged with other objects such as, for example, insertion instruments, other implants or implant devices, etc. This improved tolerance provides for more accurate insertion and/or retention of the osteoimplant at the implant site than was provided by implants prepared according to the prior art. For example, the demands presented by endoscopic surgery of the anterior spine require an implant that can be precisely and reversibly engaged with endoscopic instrumentation. Therefore, an osteoimplant manufactured to maintain close tolerances in the instrument engaging regions of the osteoimplant would be advantageous to surgeons who typically employ such devices and methods.

In a preferred form, an osteoimplant is made available to surgeons in a kit prepackaged with a delivery tool comprising means for holding the osteoimplant and then controllably releasing the osteoimplant. The delivery tool preferably includes releasable engaging means such as, for example, thread end, friction fit, multiple engagement rods, a base and a pair of flexible opposed arms extending from the base, etc. The engaging means is spaced and dimensioned to releasably hold the implant. A delivery tool handle is also provided so that the tool can be easily manipulated by the surgeon.

In the preferred kit form, the delivery tool is made of a suitable material, e.g., stainless steel, titanium alloy, sterilizable plastic, etc. The kit is provided with the osteoimplant engaged with the delivery tool, in a presterilized package. The handle of the delivery tool may also be in the package integral with the delivery tool, or may be provided separately. The osteoimplants are provided in a range of sizes for different size persons and different locations of the disk to be replaced. The surgeon makes a preoperative estimation of the range of sizes most likely to be required, and delivery tool/osteoimplant sets spanning this range are prepared for surgery. During the implant procedure, the surgeon can select the one osteoimplant that is most appropriate, and substitute another if for some reason, typically incorrect dimensions, the first choice is not operable. The surgeon need not modify the shape of the osteoimplant, but uses it directly from the package. The osteoimplant is placed into the correct position using the delivery tool, the osteoimplant is controllably released, and the delivery tool is removed and discarded. This approach minimizes the time of the operation, thereby decreasing the chances of complications for the patient.

As set forth above, the bone employed in the practice of the disclosure herein can be obtained from bone which, with respect to the final implant recipient, may be of autogenous, allogenic, xenogenic and/or transgenic origin or mixtures thereof. Porcine and bovine bones are particularly advantageous types of xenogenic bone tissue that can be used individually or in combination as sources for the bone although of course other xenogenic or transgenic bone tissues can also be used.

The monolithic section of bone preferably includes the diaphysis or metaphysis of a long bone, i.e., femur, tibia, fibula, humerus, ulna, radius; phalanges or smaller pieces, etc. obtained, for example, by making a transverse or longitudinal cut through the diaphysis or metaphysis of a long bone. Such bone sections will typically possess a total surface area of between about 100 $mm^2$ and about 10,000 $mm^2$, preferably between about 250 $mm^2$ and about 8000 $mm^2$, more preferably between about 300 $mm^2$ and about 7600 $mm^2$. After the bone is obtained from the donor and before it is subjected to a demineralizing step, it is processed, i.e., cleaned, disinfected, and defatted, etc., using methods that are conventional and well known in the art.

Methods for demineralizing the surface area of the monolithic section of bone are known. Demineralization procedures remove the inorganic mineral component of bone by employing acid solutions. Such procedures are well known in the art, see for example, Reddi et al., *Proceeding of the National Academy of Sciences of the United States of America* 69, pp. 1601–1605 (1972), incorporated herein by reference. The strength of the acid solution, the shape and size of the bone and the duration of the demineralization procedure will determine the extent of demineralization. Control of these variables to effect the desired extent of demineralization is well within the purview of those skilled in the art. Reference in this regard may be made to Lewandrowski et al., *Journal of Biomedical Materials Research,* 31, pp. 365–372 (1996).

In a preferred demineralization procedure, the osteoimplant is subjected to an acid demineralization step followed by a defatting/disinfecting step. The osteoimplant is immersed in acid over time to effect demineralization. Acids that can be employed in this step include inorganic acids such as hydrochloric acid and as well as organic acids such as formic acid, acetic acid, peracetic acid, citric acid, propionic acid, etc. The depth of demineralization into the bone surface can be controlled by adjusting the treatment time, temperature of the demineralizing solution, concentration of the demineralizing solution, and agitation intensity during treatment.

The demineralized osteoimplant is rinsed with sterile water and/or buffered solution(s) to remove residual amounts of acid and thereby raise the pH. A preferred defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. Ordinarily, at least about 10 to 40 percent by weight of water (i.e., about 60 to 90 weight percent of defatting agent such as alcohol) should be present in the defatting disinfecting solution to produce optimal lipid removal and disinfection within the shortest period of time. The preferred concentration range of the defatting solution is from about 60 to about 85 weight percent alcohol and most preferably about 70 weight percent alcohol. In accordance with this invention, demineralization is conducted to a depth of from about 100 to about 7000 microns, preferably from about 150 to about 2000 microns, and more preferably from about 200 to about 1000 microns.

In addition to the demineralizing step, the monolithic section of bone is optionally subjected to a configuring step to form the osteoimplant described herein. The configuring step can be employed using conventional equipment to produce a wide variety of geometries, e.g., threaded holes, at least two receiving holes, concave or convex surfaces, stepped surfaces, cylindrical dowels, cortical rings, wedges, blocks, screws, pins, and the like. The configuring step can also be employed to provide a vertebral interbody fusion device configured to span an intervertebral space between adjacent vertebrae.

The configuring step can be performed before and/or after the demineralizing step depending upon the intended end use of the osteoimplant and any specific properties to be imparted to the implant. It is contemplated that the configuring step, when performed after the demineralizing step, can result in the removal of some but not all of the demineralized zone(s) on the outer surface of the osteoimplant, thus selectively exposing non-demineralized bone on the outer surface of the osteoimplant. Thus, the outer surface of the osteoimplant can be provided with zones of demineralized bone as well as non-demineralized bone. These zones can be selected based on the geometry and function of the implant. For example, those surface areas of the osteoimplant that will come in direct contact with adjacent host bone tissue can be provided with demineralized zones to promote fusion with adjacent host bone tissue, whereas those surface areas that will require mechanical strength, e.g., threaded holes adapted to receive screws or surfaces adapted to mate with metallic implants, can be provided with non-demineralized zones.

When the osteoimplant is configured prior to demineralization, specific areas, cavities, holes, etc., of the osteoimplant can be treated to limit the extent of demineralization of such treated regions. For example, the treatment can consist of any suitable barrier to prevent contact of the mineralized region with the demineralizing solution. Therefore, such treatment can include "masking" agents or chemical coatings, e.g., Epon™, paraffin wax, petroleum jelly, polymeric materials that are solidifiable and substantially removable, covering the surface to remain mineralized with a dissolvable material, for example, calcium phosphate, calcium sulfate, calcium carbonate, magnesium whitlockite, Bioglass, etc. which is preferably removed prior to implantation, covering the surface to remain mineralized with a sufficient amount of a material more reactive with the demineralizing solution than bone and also doesn't dissolve readily in water and/or treatments to increase the hydrophobicity of a specific portion of the implant as well as the use of a physical barrier to occupy the cavity, hole, etc., that is desired to be maintained in a mineralized condition. For example, a threaded hole can be provided in an osteoimplant prior to demineralization. When a component such as, for example, a mating screw, a rubber or polymeric plug, etc., that is non-soluble and non-reactive with the demineralizing solution, e.g., surgical stainless steel, plastic, ceramic, etc., is screwed or inserted into the mating hole such that the region is occupied prior to demineralizing the osteoimplant, the component will prevent contact of the occupied region of the osteoimplant with the demineralizing solution and that region will therefore remain substantially mineralized and will not experience any significant change in its dimensions. An advantage of this approach to preventing undesirable demineralization as compared to coating or treating the region of the osteoimplant to remain mineralized is the ease in covering the desired area prior to demineralization, and the ease in "unmasking" the area after demineralization. Alternatively, the cutting or machining bit itself can be the masking agent if left in place in the implant during the demineralization process. Additionally, when using mechanical fasteners, the fasteners themselves can be used in the demineralization process as fixtures by which the osteoimplant is suspended in the demineralizing solution.

When the osteoimplant is configured after surface demineralization, certain advantages can be observed. For example, because any dimensional change due to demineralizing has already occurred, configuring the osteoimplant after demineralizing provides an osteoimplant which mates well with surgical instruments and other mechanical devices. This would be especially advantageous in applications where there is a need for the osteoimplant to hold tighter tolerances, e.g., a region of rigidity to hold screw threads, friction fitting the implant on an inserter that uses a press-fit attachment scheme, etc. Thus an osteoimplant that is configured after demineralizing would demonstrate improved retention of shape compared to an unmasked osteoimplant that is configured prior to demineralizing. In addition, configuring the osteoimplant after demineralizing would be beneficial in applications requiring incorporation of the implant faster in certain areas of the implant than in others.

In certain embodiments, the osteoimplant is coated and/or treated as described above to provide certain zones that remain substantially mineralized even after the osteoimplant has been exposed to demineralizing treatment. These embodiments may provide osteoimplants that are suitable for use as disclosed herein that are more easily prepared, e.g., fewer process steps, than osteoimplants requiring a configuring step to form the general shape of the implant, a demineralizing step to provide desirable biological characteristics to the implant, and a subsequent configuring step to provide desirable mineralized portions of the osteoimplant. Of course, depending upon the intended use of an osteoimplant as described herein, any suitable combination of coating and/or configuring, either before or after the step of demineralizing, may be useful according to the disclosure herein.

In a preferred embodiment, the monolithic section of bone is obtained by making a transverse cut through the diaphysis or metaphysis of a processed long bone to obtain a cylindrical portion possessing a total surface area typically ranging from about 300 to about 7500 $mm^2$, demineralizing part or all of the outer surface of the cylindrical portion to a depth of from about 100 to about 1000 microns, and configuring the surface demineralized cylindrical portion to provide an intervertebral implant. If desired, the outer surface of the intervertebral implant can be masked with an acid resistant coating or otherwise treated as described above to selectively demineralize unmasked portions of the outer surface of the intervertebral implant.

Exemplary intervertebral implants which can be fabricated by configuring the surface demineralized cylindrical portion are disclosed in U.S. patent application Ser. No. 09/328,242 entitled Ring-Shaped Intervertebral Implant, U.S. patent application Ser. No. 09/327,982 entitled Keyed Intervertebral Dowel and U.S. patent application Ser. No.

09/328,283 entitled Intervertebral Implant. Each of these applications is incorporated herein by reference. Other exemplary assembled and/or composite implants would include U.S. Pat. Nos. 5,728,159, 5,895,426, 6,025,538, and 6,200,347. Each of these patents is incorporated herein by reference.

Preferred embodiments of the presently disclosed method for preparing a partially demineralized bone graft will now be described in detail with reference to the drawings (FIGS. 1–6) in which like reference numerals designate identical or corresponding elements in each of the several views. In the presently disclosed method for preparing a partially demineralized osteoimplant, the engagement structure 12, 112, 212, which in each of these implants includes, for example, a threaded bore, is filled with a physical barrier (e.g., a plug) prior to immersing the osteoimplant in acid. As previously stated, in order to prevent demineralization from occurring, the plug is preferably formed of a material that is non-soluble and non-reactive in the demineralizing agent. Such materials may include plastics, metals, ceramics, composites, etc. Alternately, the plug may be formed of a material having a pre-selected dissolution rate or activity in acid such that a limited degree of demineralization is permitted to occur adjacent to the portion of the osteoimplant that has been plugged. In yet a further embodiment, the plug can be shaped and configured in a manner to assist in the demineralization process. For example, the plug can be perforated to allow access of the demineralization solution to certain regions of the bone. Alternatively, the plug can be configured to serve as an interface for such a pressure-flow system as described in U.S. Pat. No. 5,846,484.

The plug preferably has a shape that corresponds to the shape of the recess defining the engagement structure 12, 112, 212, of the bone graft. For example, the plug 50 may be in the form of a threaded screw (FIG. 7). Alternately, plug 50 may be frictionally retained within the engagement structure. Referring to FIG. 8, plug 50 may include a head 52 for masking the bone adjacent the engagement structure or recess that is being plugged.

The invention will be better understood by way of the following examples which are intended to illustrate but not limit the invention in anyway whatsoever.

EXAMPLE 1

Surface Demineriliztion

A study was undertaken to determine the effect of varying penetration of surface demineralization on the osteoinductive response to human cortical bone implants using an athymic rat intramuscular assay. Osteoinductivity is often defined as the ability of the agent to recruit cells to the site, and to convert them to the osteoblastic lineage. Osteoinductivity has been observed to follow an "endochondral pathway" similar to that of embryonic bone when it is first formed. This bone goes though stages, including the penetration and infiltration of cells induction of chondrogenic (cartilage-forming) cells at the site, laying down of cartilage tissue, and the transformation of that cartilage tissue to bone tissue. All of these changes can be tracked over time in histological samples.

Implants were constructed aseptically from human cortical bone. Cylindrical discs (7±1 mm in diameter and 3±0.5 mm thick) were cut from cortical bone of the same donor. Before demineralization and after cutting, the bone discs were washed in water for injection (WFI), sonicated in 70% ethanol for one hour, and washed again with WFI. The discs were surface demineralized in 0.6N HCl solution at six different time points in order to vary the demineralization layer thicknesses.

Figure 12:
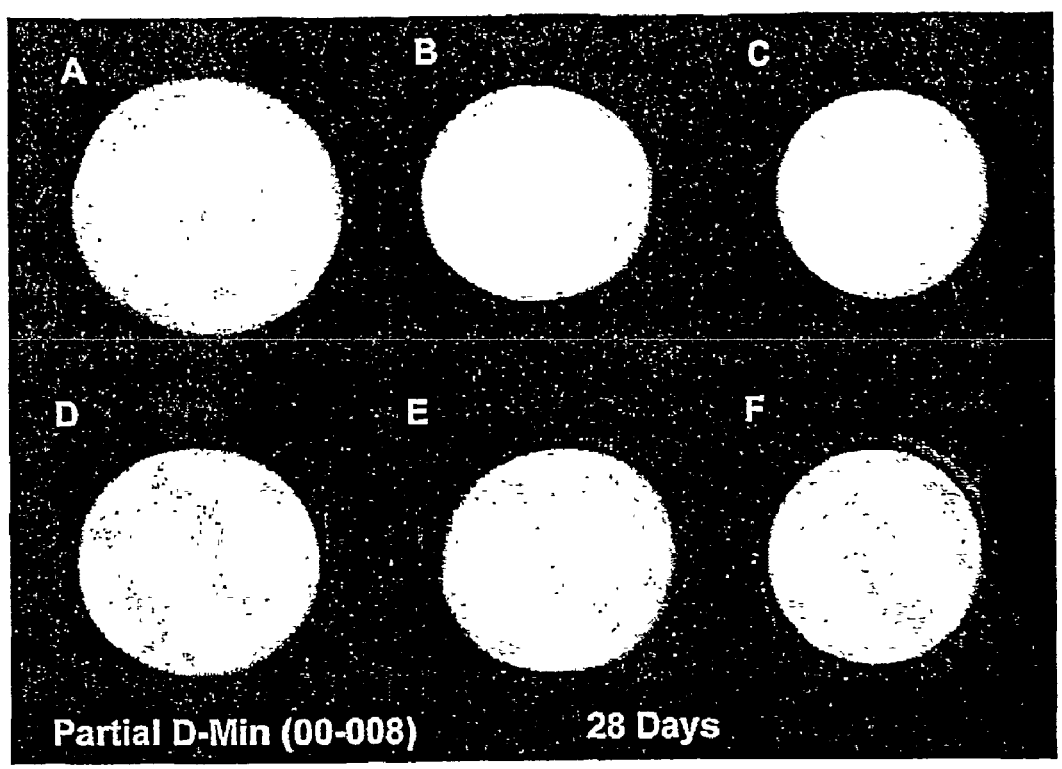
FIGS. 12–18 illustrate the osteoinductivity of bone prepared as described herein.
Figure 13:
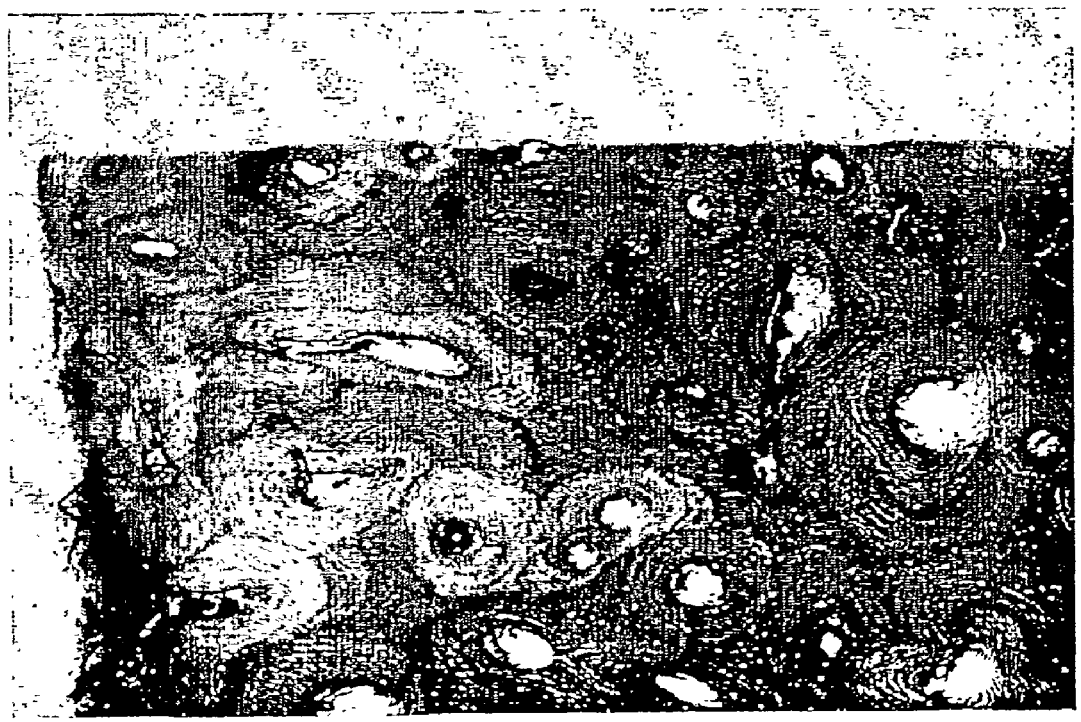
Figure 14:
Figure 15:
Figure 16:
Figure 17:
Figure 18:

Demineralization time points were A=0 hr. B=0.25 hr, C=0.5 hr, D=1 hr, E=2 hr, and F=4 hr. Ten discs were prepared in each of the 6 treatment groups. Two discs from each treatment group were reserved for initial X-rays (FIG. 12) and histomorphometry of demineralization penetration (FIGS. 13–18).

An athymic rat model was used to evaluate osteoinduction in this investigation. Standard surgical intramuscular implantation of the discs was performed on 24 rats with two implants, randomly chosen. Discs were oriented in the same manner within the musculature. Animals were sacrificed at 28 days. Each treatment group contained eight samples.

One disc from each time point was X-rayed with a Faxitron (Hewlett Packard) for 54 seconds at 50 kv. Each explanted sample was also X-rayed for 54 seconds at 50 kv.

One disc from each time point was placed in 3% basic fuchsin in order to stain the demineralized surface. Discs were cut in half down the central axis (FIG. 9), photographed, acquired with Adobe Photoshop 5.0, and analyzed with Image-Pro Plus 3.1. The actual depth of demineralization was calculated by measuring the length (pixels) of the stained demineralized area at several locations ($D_p$ and $D_r$) for each time point. The pixel measurements were averaged and converted to millimeters.

Specimens for histological analysis were harvested with attached surrounding host tissues intact to preserve the host-graft tissue interface. Half the specimens were demineralized, dehydrated, and cut in half down the central axis. Both exposed surfaces were embedded in glycol methacrylate (JB-4) and oriented to allow simultaneous sectioning of each exposed surface. Four 5-µm sections were taken at 100 µm intervals for each sample. Sections were stained with toluidine blue. Sections were microscopically evaluated to determine osteoinductive surface involvement, penetration, and overall osteoinductive response.

Figure 10:
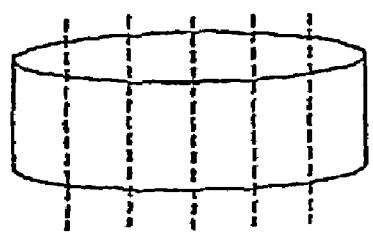

The remaining half was dehydrated and embedded in methyl methacrylate to differentiate demineralized tissues. The cylindrical test article was sectioned as shown in FIG. 10, in 1 mm increments, mounted on opaque plastic slides and hand ground when necessary.

The estimated (based upon Lewandrowski's equation for planar demineralization) and actual demineralization depths for each treatment group are listed below in Table 1.

TABLE 1

| Treatment Identification | Treatment | Demineralization Depth from Planar Surface (mm) | | Number of discs |
|---|---|---|---|---|
| | | Estimated | Actual (av.) | |
| A | 0 minutes | 0 | 0 | 10 |
| B | 15 minutes | 0.182 | 0.104 | 10 |
| C | 30 minutes | 0.257 | 0.218 | 10 |
| D | 1 hour | 0.364 | 0.419 | 10 |
| E | 2 hours | 0.515 | 0.502 | 10 |
| F | 4 hours | 0.728 | 0.657 | 10 |

Figure 11:
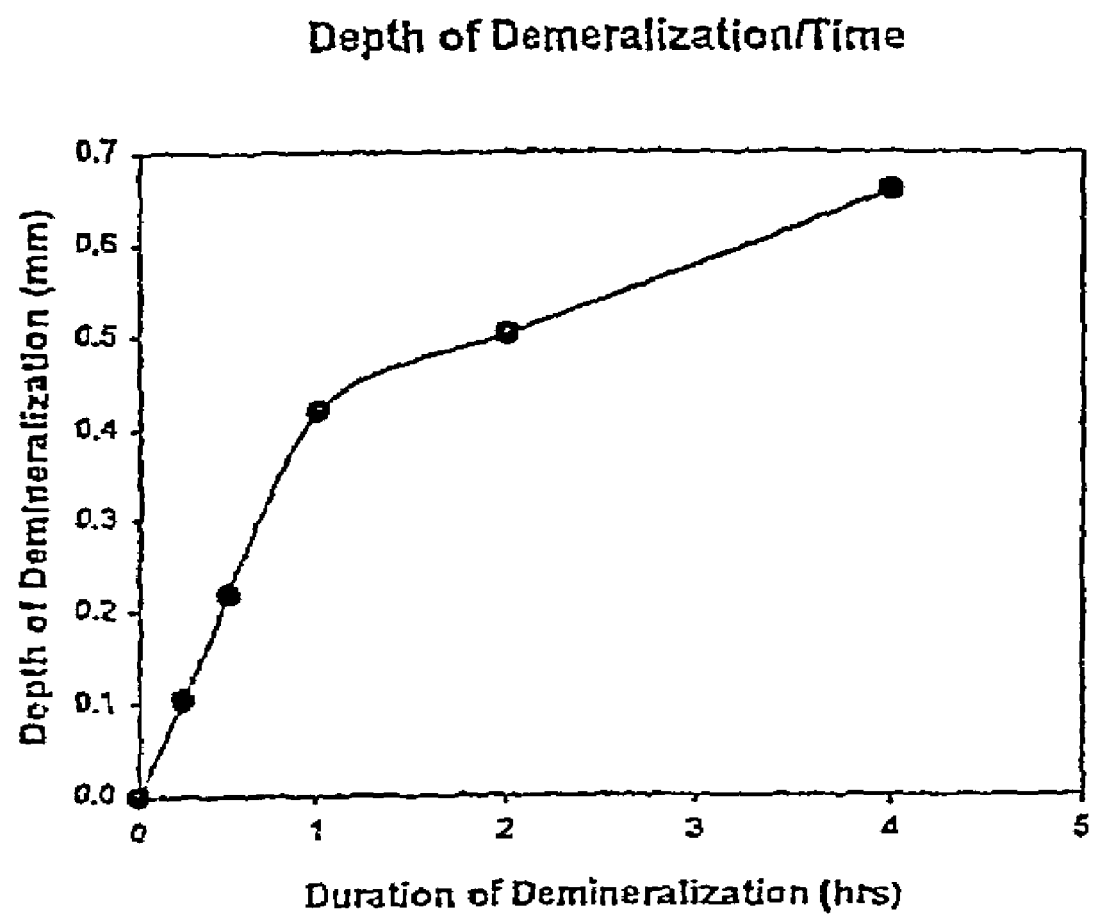
FIG. 11 is a graph demonstrating the depth of demineralization of bone as a function of the time the bone is exposed to a demineralizing solution.

The actual depths of demineralization plotted against the duration of exposure to the acid shows that the rate of surface demineralization begins to slow after one hour (FIG. 11).

The fully demineralized histology clearly shows the areas of surface demineralization. A very fine fibrous tissue layer encapsulated the discs. An inductive response, indicated by either chondrocytes or new bone formation, was evident in all of the partially demineralized samples. However, because of the fine encapsulation, this inductive response was generally limited to Haversian canals in the demineralized portion. Activity was also present in some of the canals in the mineralized portion as long as some proportion of that canal was demineralized. Therefore, the greater the depth of demineralization, the more Haversian systems are exposed, and the greater the inductive response (FIGS. 13–18).

EXAMPLE 2

Spinal Fusion Procedure

In this example, the insertion of osteoimplants having an engagement structure (12, 112, 212) in conjunction with a posterior approach for lumbar discectomy and spinal fusion will be discussed. It is to be appreciated that other surgical approaches, e.g., anterior, postero-lateral, etc., may be utilized to perform the discectomy and insert engagement structure as well.

Initially, the vertebral column is accessed via a posterior approach with the use of appropriate retractors to retract neighboring muscle tissue, blood vessels and/or nerve tissue. Thereafter, at least a portion of the disc is removed with an appropriate rongeur or cutting implements. A retractor is mounted to the posterior faces of the vertebrae. One retractor suitable for this purpose is the Cloward Lumbar Lamina Spreader manufactured by Codman. The retractor includes a pair of retractor arms which are mountable to the posterior vertebral faces via screws. With the retractor appropriately mounted, the arms of the retractor are spread to distract the adjacent vertebrae to provide adequate clearance for insertion of the osteoimplant having engagement structure between the vertebrae. The osteoimplant having engagement structure is thereafter inserted into the distracted space with an appropriate engaging instrumentation where it is received within the intervertebral space. Once the osteoimplant having engagement structure is appropriately positioned within the intervertebral space, the retractor is returned to return the adjacent vertebrae to their normal positions.

The osteoimplant having engagement structure forms a strut supporting and maintaining the adjacent vertebrae in desired spaced relation. In practice, optimum dimensions for the osteoimplant having engagement structure are determined, in part, by the dimensions of the space between the adjacent vertebrae and by the desired space if the disk height has been reduced by disease. The contact of the vertebral surfaces with the conformable demineralized surfaces of the osteoimplant having engagement structure allows for relatively rapid osteoinduction and subsequent fusion. Over a period of time, the bone tissue from adjacent vertebral bodies grow within and fuse with the osteoimplant having engagement structure to form a solid fusion.

As demonstrated in Example 1, surface demineralization elicits an inductive response on mineralized tissue. This response is proportional to the depth of demineralization. A critical depth of about 100 µm to about 200 µm has been observed to be required for initiation of osteoinduction. The rate of demineralization is greatest within the first hour of exposure to the acid solution. The 0.25 hr demineralization exposed very few Haversian canals and concurrently had minimal evidence of osteoinduction. The 0.5 hr and 1 hr time points showed a notable number of demineralized canals and therefore showed evidence of osteoinduction throughout the demineralized layer. The 2 hr and 4 hr time points do not show a noticeably greater amount of osteoinduction than the previous two time points. Since additional demineralization will degrade the implant's mechanical properties, the optimal duration of demineralization is between 0.5 hr. and 1 hr to achieve the combined biological and mechanical goals of the implant.

It will be understood that various modifications may be made to the embodiments disclosed herein. For example, the method described herein can be used to mask any recess load-bearing (or non-load-bearing) surface on a bone graft. The method is not limited to masking bone graft engagement structure. Moreover, the plug need not be cylindrical in shape but rather can be formed to correspond to the shape of any recess formed in a bone graft. Therefore, the above description should not be construed as limiting, but merely as exemplifications of preferred embodiments. Those skilled in the art will envision other modifications within the scope and spirit of the claims appended hereto.

What is claimed is:

1. A surface demineralized osteoinductive osteoimplant comprising rigid monolithic bone, the bone comprising at least one outer surface demineralized zone at least about 100 microns thick, the bone further comprising a non-demineralized core region, the non-demineralized core region being proximate to and beneath the at least one outer surface demineralized zone, wherein the non-demineralized core region is defined in at least two directions by the at least one outer surface demineralized zone.

2. The osteoimplant of claim 1, wherein, the bone is selected from the group consisting of autogenic bone, allogenic bone, xenogenic bone, transgenic bone, composites thereof, and assemblies thereof.

3. The osteoimplant of claim 1, wherein the outer surface demineralized zone is from about 100 to about 2000 microns thick.

4. The osteoimplant of claim 3, wherein the outer surface demineralized zone is from about 200 to about 1000 microns thick.

5. The osteoimplant of claim 1, wherein the outer surface demineralized zone comprises a thickness sufficient to expose osteons and provide access to Haversian canals within the bone.

6. The osteoimplant of claim 1, further comprising passageways extending from the outer surface towards the non-demineralized core region, wherein each passageway has a diameter of between about 50 and about 1000 microns.

7. The osteoimplant of claim 1, wherein the bone further comprises at least one outer surface non-demineralized zone wherein the outer surface non-demineralized zone comprises at least one engagement structure for reversible engagement with an insertion device.

8. The osteoimplant of claim 7, wherein the engagement structure has a shape selected from the group consisting of threaded holes, receiving holes, hex shaped recesses, concave surfaces, convex surfaces, stepped surfaces, tapered surfaces, flat surfaces, serrated surfaces, wedges, blocks, screws, pins, and combinations thereof.

9. The osteoimplant of claim 7, wherein the non-demineralized zone is provided by masking a region of the bone defining the non-demineralized zone prior to demineralization.

10. The osteoimplant of claim 7, wherein, the non-demineralized zone is provided by configuring at least a portion of the demineralized zone to expose the non-demineralized zone.

11. A load-bearing vertebral interbody fusion device comprising a rigid monolithic section of bone configured to span a space selected from the group consisting of an intervertebral space between adjacent vertebrae and a space between non-adjacent vertebrae, the bone comprising at least one outer surface demineralized zone for contacting the adjacent vertebra, the bone further comprising a non-demineralized core region, the non-demineralized core region being proximate to and beneath the at least one outer surface demineralized zone, wherein the non-demineralized core region is defined in at least two directions by the at least one outer surface demineralized zone.

12. The fusion device of claim 11, wherein the outer surface demineralized zone comprises a thickness sufficient to expose osteons and provide access to Haversian canals within the bone.

13. The fusion device of claim 11, further comprising passageways extending from the outer surface towards the non-demineralized core region, wherein each passageway has a diameter of between about 50 and about 1000 microns.

14. The fusion device of claim 11, wherein the bone further comprises an outer surface non-demineralized zone wherein the outer surface non-demineralized zone comprises at least one engagement structure for maintaining relatively close tolerances with an insertion instrument.

15. The fusion device of claim 14, wherein the engagement structure has a shape selected from the group consisting of threaded holes, receiving holes, hex shaped recesses, concave surfaces, convex surfaces, stepped surfaces, tapered surfaces, flat surfaces, serrated surfaces, wedges, blocks, screws, pins, and combinations thereof.

16. The fusion device of claim 14, wherein the outer surface demineralized zone is at least about 100 microns thick.

17. The fusion device of claim 16, wherein the outer surface demineralized zone is from about 100 to about 2000 microns thick.

18. The fusion device of claim 17, wherein the outer surface demineralized zone is from about 200 to about 1000 microns thick.

19. A load-bearing osteoinductive osteoimplant comprising a rigid monolithic section of bone, said bone comprising at least one outer surface demineralized zone, said bone further comprising a non-demineralized core region proximate to and beneath the at least one outer surface demineralized zone, wherein said non-demineralized core region is defined in at least two directions by the at least one outer surface demineralized zone, and wherein the outer surface demineralized zone is from about 100 to about 2000 microns thick.

20. The osteoimplant of claim 19, wherein the bone is selected from the group consisting of autograft bone, allograft bone, xenogenic bone, transgenic bone, composites thereof, and assemblies thereof.

21. The osteoimplant of claim 19, wherein the bone is obtained from a bone selected from the group consisting of diaphysis of a femur, diaphysis of a tibia, diaphysis of a fibula, diaphysis of a humerus, diaphysis of an ulna, diaphysis of a radius, metaphysis of a femur, metaphysis of a tibia, metaphysis of a fibula, metaphysis of an ulna, metaphysis of a radius, phalanges, composites thereof, and assemblies thereof.

22. The osteoimplant of claim 19, wherein the bone further comprises an engagement portion having at least one geometry selected from the group consisting of threaded holes, receiving holes, hex shaped recesses, concave surfaces, convex surfaces, stepped surfaces, cylindrical dowels, cortical rings, wedges, blocks, screws, and pins.

23. The osteoimplant of claim 22, wherein the engagement portion is substantially non-demineralized.

24. The osteoimplant of claim 19, wherein the outer surface demineralized zone is from about 200 to about 1000 microns thick.

25. The osteoimplant of claim 19, wherein the outer surface demineralized zone comprises a thickness sufficient to expose osteons and provide access to Haversian canals within the bone.

26. The osteoimplant of claim 19, further comprising passageways extending from the outer surface towards the non-demineralized core region, wherein each passageway has a diameter of between about 50 and about 1000 microns.

27. A vertebral interbody fusion device comprising a monolithic section of rigid bone configured to span an intervertebral space selected from the group consisting of an intervertebral space between adjacent vertebrae and a space between non-adjacent vertebrae, said bone comprising at least one outer surface demineralized zone, said bone further comprising a non-demineralized core proximate to and beneath the at least one outer surface demineralized zone, wherein the non-demineralized core is defined in at least two directions by the at least one outer surface demineralized zone, and wherein the outer surface demineralized zone is from about 100 to about 2000 microns thick.

28. The fusion device of claim 27, wherein the bone is selected from the group consisting of autograft bone, allograft bone, xenogenic bone, and transgenic bone.

29. The fusion device of claim 27, wherein the bone is obtained from a bone selected from the group consisting of diaphysis of a femur, diaphysis of a tibia, diaphysis of a fibula, diaphysis of a humerus, diaphysis of an ulna, diaphysis of a radius, metaphysis of a femur, metaphysis of a tibia, metaphysis of a fibula, metaphysis of an ulna, metaphysis of a radius, phalanges, composites thereof, and assemblies thereof.

30. The fusion device of claim 27, wherein the bone further comprises an engagement portion having at least one geometry selected from the group consisting of threaded holes, receiving holes, hex shaped recesses, concave surfaces, convex surfaces, stepped surfaces, cylindrical dowels, cortical rings, wedges, blocks, screws, and pins.

31. The fusion device of claim 30, wherein the engagement portion is substantially non-demineralized.

32. The fusion device of claim 27, wherein the outer surface demineralized zone is from about 200 to about 1000 microns thick.

33. The fusion device of claim 27, wherein the outer surface demineralized zone comprises a thickness sufficient to expose osteons and provide access to Haversian canals within the bone.

34. The fusion device of claim 27, further comprising passageways extending from the outer surface towards the non-demineralized core region, wherein each passageway has a diameter of between about 50 and about 1000 microns.

* * * * *